United States Patent [19]

Marti et al.

[11] Patent Number: 4,515,804

[45] Date of Patent: May 7, 1985

[54] CRYSTAL MODIFICATIONS OF (+)-CATECHIN AND PHARMACEUTICAL PREPARATIONS CONTAINING THEM

[75] Inventors: Erwin Marti; Oskar Heiber, both of Basel; Alexandre Gumma, Commugny; Gustave Huber, Crans, all of Switzerland; Isamu Utsumi; Hiroshi Nakagawa, both of Kyoto, Japan; Tatsuhiko Miyata; Koichi Akimoto, both of Osaka, Japan

[73] Assignee: Zyma SA, Nyon, Switzerland

[21] Appl. No.: 467,540

[22] Filed: Feb. 17, 1983

[30] Foreign Application Priority Data

Feb. 24, 1982 [GB] United Kingdom ............... 8205453

[51] Int. Cl.$^3$ .................. A61K 31/35; C07D 311/62
[52] U.S. Cl. ................................. 514/456; 549/399; 514/894
[58] Field of Search ................... 549/399; 424/283

[56] References Cited

PUBLICATIONS

The Merck Index, 9th ed., 1976, p. 1901.
Blum et al., Lancet, pp. 1153–1155 (1977).
Reina et al., Fortschr. Med, 96, 75 (1978).

*Primary Examiner*—Nicky Chan
*Attorney, Agent, or Firm*—Michael W. Glynn

[57] ABSTRACT

Novel crystal modifications of (+)-catechin monohydrate and of (+)-catechin anhydrate more suitable for pharmaceutical preparations for reasons of higher stability against moisture and/or light and distinguished from hitherto known modifications by unique X-ray diffraction spectra are produced by specific recrystallization and/or crystal rearrangement processes and pharmaceutical preparations comprising the novel crystal forms.

3 Claims, 5 Drawing Figures

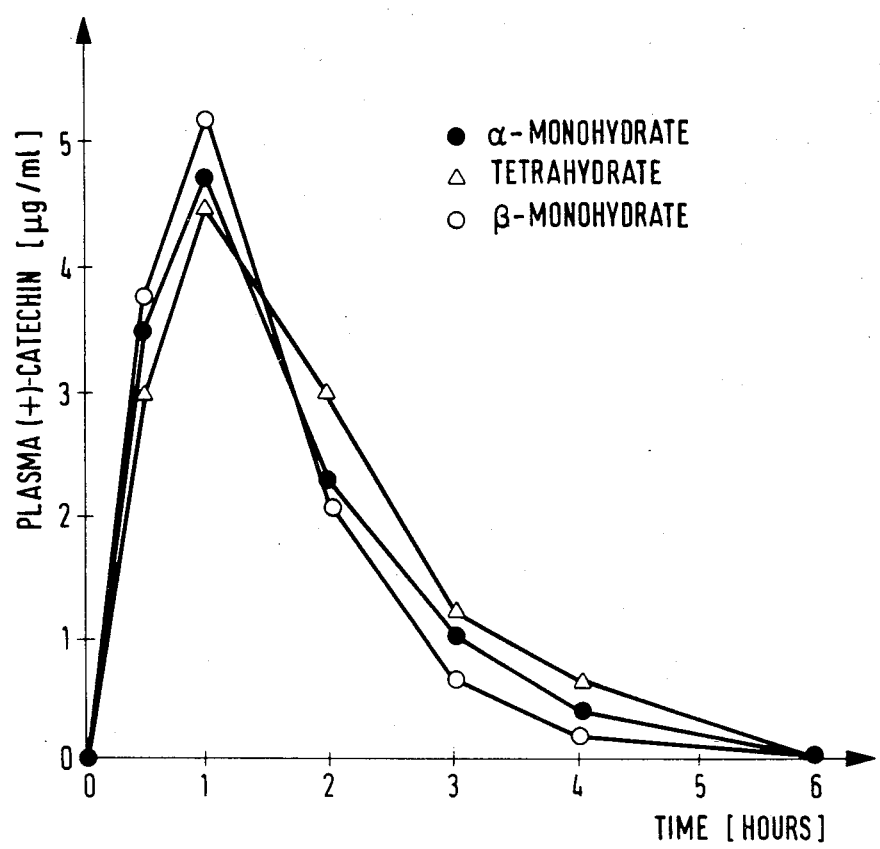

CRYSTAL MODIFICATIONS OF (+)-CATECHIN AND PHARMACEUTICAL PREPARATIONS CONTAINING THEM

The present invention relates to novel crystal modifications of the monohydrate and the anhydrous form of (+)-catechin, to processes for their preparation, and to pharmaceutical preparations comprising said compounds.

(+)-Catechin is a compound of the formula

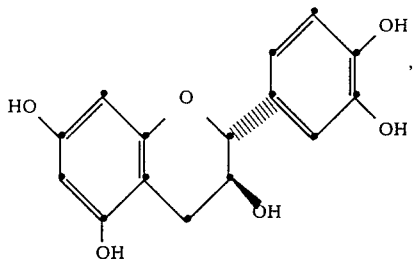

and can be named (2R,3S)-2-(3,4-dihydroxyphenyl)-3,4-dihydro-2H-1-benzopyran-3,5,7-triol, (2R,3S)-5,7,3′,4′-tetrahydroxy-flavanol-3or (2R,3S)-3,3′,4,4′,5,7-pentahydroxyflavan. It is also called d-catechin and (+)-cyanidanol-3, or incorrectly d-catechol, d-catechinic acid, d-catechuic acid, or d-cyanidol, whereby the "d-" indicating the (+)-form is not always used.

The compound is found primarily in higher wooden plants along with (−)-epicatechin and is for industrial purposes obtained mainly by extracting leaves and branches of Uncaria gambir or wooden parts of Acacia catechu with hot water, evaporating the extract and purifying the resulting residue, the so-called block gambir and the acacia catechu, respectively, further by recrystallisation from water and drying the crystals (The Merck Index, 9th Ed., 1976, p.1901). (+)-Catechin is an astringent and is therapeutically used for the treatment of liver diseases (see Lancet ii, 1153–1155, (1977), and Fortschritte der Medizin, 92, 75–79 (1978)).

It has been known previously that (+)-catechin is available in crystalline form such as a tetrahydrate, a monohydrate or in anhydrous form (see R. Clauser, Chemische Berichte,36, 101–107, 1903). It is generally accepted that recrystallisation of crude catechin from water followed by air drying at room temperature gives (+)-catechin tetrahydrate (melting point 96° C., abbreviated designation in the present description: "tetrahydrate") which changes to the known (+)-catechin monohydrate (melting point 176° C., abbreviated designation in the present description: "β-monohydrate") on drying over sulfuric acid at room temperature, and drying of the β-monohydrate at 100° C. under atmospheric pressure gives the known anhydrous form of (+)-catechin (melting point 210° C.; abbreviated designation in the present description: "η-anhydrate").

H. L. Hergert and E. F. Kurth, Journal of Organic Chemistry, 18, 251 (1953) reported the X-ray diffraction spectra of the low melting form (melting point 176°–177° C.) and the high melting form (melting point 219° C.) obtained from crude (3❍)-catechin. The present inventors have found, from a comparison of the X-ray diffraction patterns of the β-monohydrate and the η-anhydrate produced according to the method described in the Berichte article, that regarding the two forms described in the Journal of Organic Chemistry article, the low melting form is a mixture of the β-monohydrate and the η-anhydrate described in the Berichte article, and the high melting form corresponds to the η-anhydrate described in the Berichte article.

The known crystal forms of the tetrahydrate, the β-monohydrate and the η-anhydrate of (+)-catechin can be distinguished by their different X-ray diffraction spectra (e.g. obtained by using $Cu:K_{\alpha 1}$-rays), and also by thermogravimetry, whereby the loss of water upon heating of a sample at a rate of 5° C. per minute in a normal air atmosphere at discrete temperatures is gravimetrically determined.

The following lattice distances in Angstrom (Å) of the X-ray diffraction spectra of the various crystalline powders are obtained by recording the diffraction lines of the $Cu:K_{\alpha 1}$-rays ($\lambda = 1{,}5405$ Å) on a film with the aid of a Guinier IV camera. As a standard there is used α-quartz the d-values of which are calculated from $a_o = 4.913$ Å and $c_o = 5.405$ Å. The relative intensities of the lines are estimated by inspection with the eyes.

The X-ray diffraction spectrum of the tetrahydrate is characterised by the following eleven main diffraction lines:

| Lattice Distance in Å | Relative Intensities |
| --- | --- |
| 16.3 ± 0.3 | strong |
| 11.1 ± 0.1 | very strong |
| 6.40 ± 0.06 | medium |
| 5.32 ± 0.05 | strong |
| 4.56 ± 0.04 | strong |
| 4.25 ± 0.04 | medium |
| 3.95 ± 0.03 | medium |
| 3.76 ± 0.03 | very strong |
| 3.43 ± 0.02 | very strong |
| 3.22 ± 0.02 | strong |
| 3.12 ± 0.02 | strong |

The X-ray diffraction spectrum of the tetrahydrate is furthermore characterised by having in addition to said eleven diffraction lines the following six diffraction lines:

| Lattice Distance in Å | Relative Intensities |
| --- | --- |
| 4.68 ± 0.04 | medium |
| 4.22 ± 0.04 | medium |
| 4.04 ± 0.04 | medium |
| 3.92 ± 0.03 | medium |
| 3.26 ± 0.02 | medium |
| 3.05 ± 0.02 | medium |

The X-ray diffraction spectrum of the β-monohydrate is characterised by having the following twelve main diffraction lines:

| Lattice Distance in Å | Relative Intensities |
| --- | --- |
| 10.70 ± 0.10 | medium |
| 9.60 ± 0.10 | medium |
| 6.30 ± 0.06 | medium |
| 5.35 ± 0.05 | very strong |
| 5.00 ± 0.05 | medium |
| 4.53 ± 0.05 | very strong |
| 4.19 ± 0.04 | medium |
| 4.00 ± 0.03 | medium |
| 3.82 ± 0.03 | medium |
| 3.56 ± 0.03 | medium |
| 3.41 ± 0.02 | very strong |
| 3.09 ± 0.02 | medium |

The X-ray diffraction spectrum of the β-monohydrate is furthermore characterised by having in addition to said twelve diffraction lines the following five diffraction lines:

| Lattice Distance in Å | Relative Intensities |
| --- | --- |
| 4.62 ± 0.05 | medium |
| 4.31 ± 0.03 | weak |
| 3.36 ± 0.02 | medium |
| 3.23 ± 0.02 | medium |
| 3.19 ± 0.02 | medium |

The β-monohydrate is furthermore characterized by the above mentioned thermogravimetric method as follows:

| Temperature in °C. | Weight Loss as Water in % |
| --- | --- |
| 40 | 0.3 ± 0.10 |
| 50 | 0.6 ± 0.15 |
| 60 | 1.1 ± 0.20 |
| 70 | 1.6 ± 0.25 |
| 80 | 2.2 ± 0.30 |
| 90 | 3.3 ± 0.35 |
| 100 | 4.5 ± 0.40 |
| 110 | 5.3 ± 0.40 |
| 120 | 5.7 ± 0.50 |
| 130 | 5.9 ± 0.50 |
| 140 | 6.0 ± 0.50 |
| 150 | 6.0 ± 0.50 |
| 160 | 6.0 ± 0.50 |
| 180 | 6.1 ± 0.50 |

The maximum evaporation rate under the given conditions for the β-monohydrate is observed at a temperature of 93° C.

The X-ray diffraction spectrum of the η-anhydrate is characterized in agreement with literature values (H. L. Hergert et al. above) by having the following nine diffraction lines:

| Lattice Distance in Å | Relative Intensities |
| --- | --- |
| 11.50 ± 0.20 | strong |
| 5.76 ± 0.06 | strong |
| 4.45 ± 0.05 | medium |
| 4.10 ± 0.04 | medium |
| 3.95 ± 0.04 | medium |
| 3.72 ± 0.04 | weak |
| 3.59 ± 0.04 | very weak |
| 3.47 ± 0.03 | medium |
| 3.34 ± 0.03 | weak |

The η-anhydrate is furthermore characterized by the above mentioned thermogravimetric method as follows:

| Temperature in °C. | Weight Loss as Water in % |
| --- | --- |
| 30 | 0.4 |
| 40 | 0.5 |
| 50 | 0.8 |
| 60 | 1.0 |
| 70 | 1.2 |
| 80 | 1.3 |
| 90 | 1.4 |
| 100 | 1.5 |
| 120 | 1.5 |
| 140 | 1.5 |
| 160 | 1.5 |

The maximum of the evaporation rate under the given conditions for the η-anhydrate is observed at a temperature of 50° C.

The water content of the β-anhydrate is due to the strong hygroscopicity. This observation is in agreement with the literature (H. L. Hergert et al. above).

Investigations of the present inventors have shown that the tetrahydrate produced by the method described in the Berichte article cited above changes to the β-monohydrate at room temperature in the absence of a dehydrating agent, such as sulfuric acid, if placed in an atmosphere having a low moisture content (water content), and that these tetrahydrate, β-monohydrate and η-anhydrate change to each other at room temperature depending upon the moisture content of the ambient atmosphere.

For example, as FIG. 4 of the accompanying drawings shows, at a temperature of 20° C., the η-anhydrate changes to the β-monohydrate at a relative humidity of more than about 10%; the β-monohydrate to the tetrahydrate at a relative humidity of more than about 40%; and the tetrahydrate to the β-monohydrate at a relative humidity of less than about 70% (see Referential Example 1 and FIG. 4).

Thus, the known (+)-catechin crystal forms have serious disadvantages, particularly in the manufacture of the pharmaceutical preparations containing them, because their degree of hydration changes at ordinary temperatures with the variations of the moisture content of the ambient atmosphere. The resulting changes of the degree of hydration during the manufacturing process of the pharmaceutical compositions can cause variations in the (+)-catechin content of the pharmaceutical preparations, which content has to be accurate. The effects of the changes of the degree of hydration are serious, as can be seen from the fact that, for example, 1 g of the β-monohydrate corresponds to 1.17 g of the tetrahydrate.

Furthermore, the variations in the hydration state of (+)-catechin require a strict control of the ambient moisture during storage of the bulk, or during manufacture and storage of the various types of pharmaceutical preparations (e.g., powders, tablets etc.). For example, tablets containing β-monohydrate tend to swell with increasing moisture during storage, and consequently are deformed or show a decrease in hardness (see Example 1 and Table 3 given hereinbelow). It should be noted that the known crystal forms have an unpleasant bitter taste which makes them less acceptable upon oral administration. In order to mask the taste tablets consisting of those known crystal have to be coated. Obviously, there existed a strong need to improve the quality of the active substance and to overcome the difficulties caused by the known crystal forms.

It has now been found that the novel crystal form of (+)-catechin monohydrate (abbreviated designation in this specification: "α-monohydrate") and the two novel crystal forms of anhydrous (+)-catechin (abbreviated designation in this specification: "γ-anhydrate" and "δ-anhyrate"), which new crystal forms are different from those of the conventional β-monohydrate and η-anhydrate and are free or substantially free from known crystalline forms of (+)-catechin, unexpectedly satisfy these needs. Thus, the new α-monohydrate shows highly improved stability against temperature, moisture and light, and the novel γ- and especially the the novel δ-anhydrate are much more stable, especially against moisture, as compared to the known η-anhydrate.

It is an object of this invention to provide a novel crystal modification of (+)-catechin monohyrate (designated α-monohydrate) which is stable to temperature, moisture and light and has less bitter taste. Another object of this invention is to provide a process for producing this α-monohydrate. Still another object of the invention is to provide a solid pharmaceutical preparation comprising this α-monohydrate.

Further objects of the present invention are to provide two novel crystal modifications of anhydrous (+)-catechin (designated γ-anhydrate and δ-anhydrate), which are more stable than the hitherto known η-anhydrate, to provide processes for the production of these novel crystal modifications, and to provide pharmaceutical preparations comprising these novel anhydrous crystal modifications.

Accordingly this invention concerns a novel crystal modification of (+)-catechin monohydrate (designated α-monohydrate) characterized by having at least the following nine lattice distances and relative line intensities in its X-ray diffraction spectrum obtained by using Cu:$K_{\alpha 1}$-rays:

| Lattice Distance in Å | Relative Intensities |
| --- | --- |
| 7.17 ± 0.10 | very strong |
| 6.17 ± 0.06 | medium |
| 5.95 ± 0.06 | medium |
| 4.49 ± 0.04 | strong |
| 4.20 ± 0.04 | strong |
| 3.84 ± 0.03 | strong |
| 3.65 ± 0.03 | very strong |
| 3.41 ± 0.02 | medium |
| 3.24 ± 0.02 | medium |

The errors of the single measurements for the lattice distances in above X-ray diffraction spectrum, and in all the other X-ray diffraction spectra in this specification as well, are presented in terms of confidence intervals on a 68% level.

Preferably, the (+)-catechin monohydrate in the aforesaid novel α-form, in addition to the aforesaid nine diffraction lines, further has the following eight diffraction lines and relative intensities:

| Lattice Distance in Å | Relative Intensities |
| --- | --- |
| 4.39 ± 0.04 | medium |
| 4.13 ± 0.04 | strong |
| 3.97 ± 0.03 | medium |
| 3.78 ± 0.03 | medium |
| 3.75 ± 0.03 | medium |
| 3.58 ± 0.03 | medium |
| 3.37 ± 0.02 | medium |
| 3.19 ± 0.02 | medium |

The novel crystal form of the monohydrate (α-monohydrate) differs from the hitherto known monohydrate crystal form (β-monohydrate) as is evident from a comparison of the two X-ray diffraction spectra.

The novel α-monohydrate is furthermore characterized, and can be distinguished from the β-monohydrate, by the above thermogravimetric method. The loss of water in normal atmosphere measured at a scanning rate of 5° C. per minute is given for various raising temperatures in the following table:

| Temperature in °C. | Weight Loss as Water in % |
| --- | --- |
| 40 | 0.02 ± 0.03 |
| 50 | 0.02 ± 0.03 |
| 60 | 0.04 ± 0.03 |
| 70 | 0.06 ± 0.03 |
| 80 | 0.09 ± 0.05 |
| 90 | 0.16 ± 0.10 |
| 100 | 0.25 ± 0.15 |
| 110 | 0.47 ± 0.20 |
| 120 | 1.16 ± 0.25 |
| 130 | 2.60 ± 0.40 |
| 140 | 4.33 ± 0.40 |
| 150 | 5.48 ± 0.40 |
| 160 | 5.65 ± 0.40 |
| 170 | 5.68 ± 0.40 |
| 180 | 5.73 ± 0.40 |

The error of the mean values for the loss of water under the given conditions in the case of α- and β-monohydrate are represented in terms of confidence intervals on a 68% level.

The maximum of the water evaporation rate for the α-monohydrate under the given conditions is observed at a temperature of 130° C.

Both the α- and the β-monohydrate have identical elemental analysis values ($C_{15}H_{14}O_6 \cdot H_2O$), water content, UV spectrum, thin-layer chromatogram, gas chromatogram and specific rotation.

Unexpectedly, the novel α-monohydrate is more stable to temperature, moisture (water) and light than the known β-monohydrate as will be shown below.

These unexpected advantages of the α-monohydrate over the β-monohydrate and other known forms and their implications for the preparation of pharmaceutical preparations are discussed in detail further below.

The process for the production of the novel (+)-catechin α-monohydrate having the X-ray diffraction spectrum indicated above comprises:

(a) seeding an aqueous solution supersaturated solely with respect to (+)-catechin, α-monohydrate with crystals of (+)-catechin α-monohydrate, allowing the (+)-catechin α-monohydrate to crystallize, and collecting the (+)-catechin α-monohydrate, or (b) maintaining a solid (+)-catechin differing from the α-monohydrate form, or a mixture thereof with another solid form (+)-catechin at a temperature of between about 50° to about 140° C. in the presence of water and collecting the (+)-catechin α-monohydrate.

Process (a): The aqueous solution supersaturated solely with respect to (+)-catechin α-monohydrate is an aqueous solution wherein the concentration of (+)-catechin at any given crystallisation temperature is above the solubility curve of (+)-catechin α-monohydrate but below the the solubility curve of any other (+)-catechin crystal form, especially below the solubility curve of (+)-catechin tetrahydrate or (+)-catechin β-monohydrate, in the given solvent.

This aqueous supersaturated solution may be prepared by dissolving any of the known forms of this compound, e.g. the tetrahydrate, the β-monohydrate or the η-anhydrate, or any suitable new form of the present application, i.e. the γ-or δ-anhydrate, or mixtures of different crystalline forms of (+)-catechin or its hydrates, including mixtures with the α-monohydrate in water, or in a mixture of water and an organic solvent at room temperature or at elevated temperature, e.g. up to the boiling point of the solvent used, avoiding or eliminating any seed crystals or other crystallisation germs, and bringing the obtained clean solution into the state of supersaturation as described below. If a mixture of water and an organic solvent is desired, the compound is preferably dissolved in the organic solvent and water is then added. Solvents which can be used are those, in which the (+)-catechin starting material is soluble. Such solvents are especially polar solvents, such as alcohols, especially lower alkanols, for example, methanol, ethanol or propanol, liquid acids, such as corresponding lower alkanoic acids, for example, formic or especially acetic acid, ketones, especially lower alkanones, for example, acetone or methyl ethyl ketones, esters, such as lower alkyl alkanoates, for example, ethyl acetate, ethers, such as di-lower alkyl ethers or dioxacycloalkane compounds, for example, diethyl ether or dioxane, amides, such as N-lower alkyl substituted alkanoic acid amides, especially formamides, for example dimethyl formamide, nitriles, especially of lower alkanoic acids, for example acetonitrile, and the like. During the course of the crystallization prior to it, the solvent may be distilled off in order to increase the state of supersaturation of the aqueous solution. The concentration of the supersaturated starting solution may vary in a wide range. For practical purposes the supersaturated starting solution contains, for example from about 1% to about 50%, preferably from about 10% to about 20% of anhydrous (+)-catechin.

It is to be understood that in process (a) the state of supersaturation is to be attained is one with respect to the α-monohydrate. The supersaturated solution can be obtained by cooling an optionally warm saturated solution of the compound free of any particles, which may cause crystallization, or by adding a solvent, in which the desired crystalline α-monohydrate is less soluble, to a solution of the (+)-catechine in a solvent, wherein it is well soluble, or by distilling of the solvent or solvent mixture, or by saturating the solvent or solvent mixture with a crystal form which is more soluble than the desired crystal form. Any of these methods may also be combined.

Preferably, a form of the (+)-catechin which is more soluble than the α-monohydrate, especially the tetrahydrate, is dissolved in water at a temperature of between about 50° and about 90° C., preferably at about 80° C., in such an amount that a saturated solution is obtained, and this saturated solution is cooled to room temperature after seeding it with crystals of the α-monohydrate. The cooling process should be performed slowly enough, so as to ensure the crystallization of the α-monohydrate alone. If the crystallization mixture is cooled too fast, the danger exists that any of the other forms, especially the β-monohydrate and/or the tetrahydrate, crystallizes out simultaneously.

The seed crystals of the α-monohydrate can be obtained according to process (b), or otherwise prepared in situ in the crystallization mixture according to the modification of process (b), wherein any solid non-α-monohydrate-form of (+)-catechin is maintained at a temperature between about 50° to about 140° C. in water. For example, an aqueous solution of (+)-catechin, supersaturated with respect to the α-monohydrate, may be cooled down quickly until some of the tetrahydrate or β-monohydrate or a mixture thereof crystallizes, whereupon the crystallization mixture is maintained at the above temperature, if necessary, after heating preferably at between about 50° and 90° C., or more specifically at between about 60° and about 80° C. During this prolonged maintainance at that temperature, the intermediate crystal forms will rearrange into the desired α-monohydrate and as soon as sufficient seed crystals of the α-monohydrate are present cooling is continued. The seed crystals are advantageously, applied in finely powdered form, preferably in a particle size below 10 μm, and in an high enough amount that only the α-monohydrate crystallizes. The amount of seed crystals may vary in wide ranges. In general an amount of about 0.1% to about 10%, preferably of about 1% to about 3%, of seed crystals is sufficient.

The process may be performed in a vessel under atmospheric pressure, or, if more than 100° C. are required, in a closed vessel under pressure.

The resulting (+)-catechin α-monohydrate is collected from the crystallisation mixture by known methods, such as filtration, centrifugation and the like, washed, if desired, with e.g. water, and dried at a temperature of about 50° to about 100° C., if desired under reduced pressure, and for a length of time, which assures that the one mole of crystal water present in the α-monohydrate is not removed.

Process (b): The solid (+)-catechin differing from the α-monohydrate, which may be used in this process are the known tetrahydrate, β-monohydrate or η-anhydrate, or the new γ- or δ-anhydrate described further below; mixtures of solid forms of (+)-catechin used as starting materials, include mixtures of the above forms with the α-monohydrate. The starting materials are maintained under the given conditions in solid form, e.g. in the form of suspensions in any suitable water containing solvent, e.g. any of the aqueous solvent mixtures mentioned in process (a), or preferably in water, in the form of a dry powder, or in molten form. The water present may be in the form of or part of the liquid phase of the suspension, or in the form of a water-containing gaseous phase with a relative humidity preferably of at least 50%. The gaseous phase consists preferable of the ambient atmosphere, i.e. air, but also of an inert gas, e.g. nitrogen, or mixtures of different gases or of gases with air.

A suspension, e.g. the aqueous suspensions of the starting material may be allowed to stand or stirred during the heating period. In order to maintain temperatures above 100° C., a closed pressure vessel may have to be used.

The suspension, e.g. the aqueous suspension, or the gaseous phase, in which the starting material is maintained, is preferably kept at a temperature of about 50° to about 90° C., especially at a temperature of about 60° to about 80° C. The gaseous phase has preferably a relative humidity of about 70 to about 90%.

To maintain the starting material as a powder in the above atmosphere, the material may be left to stand in the atmosphere within a closed vessel, or a stream of the gaseous phase may be passed through the starting material kept in an open system. The simplest method is to form the aforesaid gaseous phase by a constant temperature-humidity device and allow the starting material to remain in it.

The molten form is preferably produced from the tetrahydrate by heating the latter above its melting point, i.e. above 96° C., especially up to about 140° to about 160° C., particularly up to about 150° C., at which the tetrahydrate loses part of its water.

The conversion of the starting material to the α-monohydrate can be promoted and made uniform by pulverizing the starting material, admixing some seed crystals of the (+)-catechin α-monohydrate and suspending the powder in the aqueous suspension phase or spreading the powder in the form of a layer having a thickness of up to about 15 cm, preferably from about 2 cm to about 10 cm, and occasionally agitating the suspension or the powder layer. To the molten form, seed crystals are advantageously added after about 3 moles of the water content present in the tetrahydrate have evaporated.

The time required for heating the starting material varies depending upon the type of starting material used, the temperature of the suspension or the temperature and relative humidity of the gaseous phase. It varies from a few minutes up to about 300 hours, and is usually from about 12 to about 35 hours in the case of suspensions and the dry powder and from a few minutes up to a few hours in the case of the molten form.

The $\eta$-, $\gamma$- and $\delta$-anhydrates may need some more time, because these anhydrates are first to be converted to the monohydrate or eventually to the tetrahydrate form. When anhydrates are used as starting materials, the relative humidity of a gaseous phase is preferably at least 80% and the temperature of about 50° to about 70° C.

For recovering the $\alpha$-monohydrate from the suspension, the same methods may be applied as mentioned under process (a).

The $\alpha$-monohydrate, whenever obtained according to the preferred process (a) or from the preferred suspension procedure according to process (b), has a very mild and much less bitter taste than the known $\beta$-monohydrate.

The preparation of the known starting materials, the tetrahydrate, the $\beta$-monohydrate and the $\eta$-anhydrate, is performed in conventional manner. For example the tetrahydrate is obtained by extracting leaves and branches of Ungaria gambir or wooden parts of Acacia catechu with water, evaporating the water extract to a water content of at most 15%, and recrystallizing the obtained so called blocgambir which contains mainly the tetrahydrate of (+)-catechin from various solvents and/or from water. The $\beta$-monohydrate may be obtained by drying the tetrahydrate over sulfuric acid or other drying agents, whereby three moles of water are lost, or drying at elevated temperatures up to 120° C. and/or with dry air, dry nitrogen or other drying agents. The $\eta$-anhydrate is obtained from either the tetrahydrate or the $\beta$-monohydrate upon further drying or by recrystallizing an aqueous solution of (+)-catechin at 38° to 40° C. (Beilstein 17, p. 211 and 17/3+4, p. 3842).

The novel $\gamma$- and $\delta$-anhydrate of (+)-catechin, which are free or substantially free of crystal water, processes for their preparation and pharmaceutical preparations containing these compounds are further objects of the present invention.

The novel $\gamma$-anhydrate of (+)-catechin, which is free or substantially free of water, is characterized by having at least the following nine lattice distances and relative line intensities in the X-ray diffraction spectrum obtained by using $Cu:K_{\alpha 1}$-rays:

| Lattice Distance in Å | Relative Intensities |
|---|---|
| 10.0 ± 0.1 | strong |
| 6.23 ± 0.06 | medium |
| 5.60 ± 0.06 | very strong |
| 5.00 ± 0.05 | strong |
| 4.63 ± 0.05 | very strong |
| 4.00 ± 0.03 | very strong |

-continued

| Lattice Distance in Å | Relative Intensities |
|---|---|
| 3.81 ± 0.03 | very strong |
| 3.62 ± 0.03 | strong |
| 3.25 ± 0.02 | strong |

The X-ray diffraction spectrum of the $\gamma$-anhydrate is furthermore characterized by having in addition to the above given eleven lattice distances and relative intensities the following six lattice distances and relative intensities:

| Lattice Distance in Å | Relative Intensities |
|---|---|
| 4.72 ± 0.05 | medium |
| 3.24 ± 0.02 | strong |
| 3.16 ± 0.02 | weak |
| 3.15 ± 0.02 | weak |
| 3.10 ± 0.02 | weak |
| 3.01 ± 0.02 | weak |

The $\gamma$-anhydrate is furthermore characterized by the above mentioned thermogravimetric method as follows:

| Temperature in °C. | Weight Loss as Water in % |
|---|---|
| 30 | 0 |
| 40 | 0.1 |
| 50 | 0.2 |
| 60 | 0.3 |
| 70 | 0.4 |
| 80 | 0.4 |
| 90 | 0.4 |
| 100 | 0.5 |
| 120 | 0.5 |
| 140 | 0.5 |
| 160 | 0.6 |

The X-ray diffraction pattern of the $\gamma$-anhydrate differs from that of the $\eta$-anhydrate, and thus, the two differ from each other in crystal form.

The $\gamma$-anhydrate agrees with the $\eta$-anhydrate of (+)-catechin ($C_{15}H_{14}O_6$) in elemental analysis values and water content, and completely agrees also in thin-layer chromatogram and specific rotatation.

The process for the preparation of the novel (+)-catechin $\gamma$-anhydrate comprises (c) maintaining the $\beta$-monohydrate at a temperature of about 100° to about 130° C. and a relative humidity of up to about 20% and collecting the (+)-catechin $\gamma$-anhydrate, or (d) heating the (+)-catechin tetrahydrate at a temperature of above its melting point up to about 180° C., seeding, or not seeding the molten form with seed crystals of the (+)-catechin $\gamma$-anhydrate and collecting the (+)-catechin $\gamma$-anhydrate, or (e) heating (+)-catechin $\eta$-anhydrate between about 130° and about 180° C. for at least 15 minutes at a relative humidity of about zero and collecting the (+)-catechin $\gamma$-anhydrate.

According to process (c) the heating time is from about 50 to about 150 hours depending on the temperature. Preferably the starting material is heated for about 50 to 80 hours, especially about 70 hours at a temperature of about 110° to 130° C., especially about 112° C., the relative humidity at the end of the experiment being from about 0% to about 20%.

According to process (d), the starting material is heated above about 96° C. (the melting point of the tetrahydrate), and preferably higher, up to about 140° to 150° C., allowing the water to evaporate, and the molten phase is seeded before the η-anhydrate starts to crystallize with the seed crystals of the (+)-catechin γ-anhydrate. Stirring may be of advantage. The time required depends on the amount of starting material used. Preferably a wet tetrahydrate is used as starting material.

(e) According to process (e), the starting material is heated preferably at a temperature of about 150° to about 170° C. The heating time varies from about 15 minutes to about 3 hours or longer and depends on the temperature. At the preferred temperature a heating time of about 30 minutes is sufficient. The heating is preferably performed under exclusion of moisture, i.e. at a relative humidity of zero or near to zero. A drying oven may be used with advantages.

The novel δ-anhydrate of (+)-catechin, which is free or substantially free of water, is characterized by having at least the following eleven lattice distances and relative line intensities in the X-ray diffraction spectrum obtained by using $Cu:K_{\alpha 1}$-rays:

| Lattice Distance in Å | Relative Intensities |
| --- | --- |
| 7.7 ± 0.1 | medium |
| 7.50 ± 0.06 | weak |
| 6.50 ± 0.06 | weak |
| 5.17 ± 0.05 | weak |
| 4.87 ± 0.05 | medium |
| 4.60 ± 0.05 | strong |
| 4.43 ± 0.04 | strong |
| 4.00 ± 0.04 | medium |
| 3.86 ± 0.04 | very strong |
| 3.28 ± 0.02 | medium |
| 3.15 ± 0.02 | strong |

The X-ray diffraction spectrum of these δ-anhydrate is furthermore characterized by having in addition to the above given eleven lattice distances and relative intensities the following six lattice distances and relative intensities:

| Lattice Distance in Å | Relative Intensities |
| --- | --- |
| 4.78 ± 0.05 | medium |
| 4.55 ± 0.05 | medium |
| 3.97 ± 0.04 | medium |
| 3.09 ± 0.02 | weak |
| 3.02 ± 0.02 | weak |
| 3.00 ± 0.02 | very weak |

The δ-anhydrate is furthermore characterized by the above mentioned thermogravimetric method as follows:

| Temperature in °C. | Weight Loss as Water in % |
| --- | --- |
| 30 | 0 |
| 40 | 0 |
| 50 | 0.1 |
| 60 | 0.1 |
| 70 | 0.1 |
| 80 | 0.2 |
| 90 | 0.2 |
| 100 | 0.2 |
| 120 | 0.2 |
| 140 | 0.3 |
| 160 | 0.3 |

The X-ray diffraction spectrum of the δ-anhydrate differs from that of η-anhydrate and the γ-anhydrate, and thus has a novel crystal form.

The novel δ-anhydrate agrees with the η-anhydrate and the γ-anhydrate of (+)-catechin ($C_{15}H_{14}O_6$) in elemental analysis values, and also in UV-spectrum, thin-layer chromatogram, gas chromatogram and specific rotation (see Example 5 and Table 2 hereinbelow).

The novel process for the preparation of the (+)-catechin δ-anhydrate comprises:

(f) maintaining the η-anhydrate at a temperature of about 100° C. to about 130° C. and a relative humidity of up to 20% and collecting the (+)-catechin δ-anhydrate, or (g) heating the (+)-catechin tetrahydrate at a temperature of above its melting point to about 180° C., seeding or not seeding the molten form with seed crystals of the (+)-catechin δ-anhydrate and collecting the (+)-catechin δ-anhydrate, or (h) heating the (+)-catechin β-monohydrate at a temperature between about 50° to about 90° C. at a relative humidity up to 20% and collecting the (+)-catechin δ-anhydrate.

According to process (f) the heating time is from about 10 to about 100 hours depending on the temperature. Preferably, the starting material is heated for about 10 to 30 hours, especially about 23 hours, at a temperature of about 100° to 120° C., especially about 112° C., the relative humidity at the end of the experiment being from about 10 to about 20%.

According to process (g) the starting material is heated above about 96° C. (the melting point of the tetrahydrate) and preferably higher, up to about 140° to 150° C., allowing the water to evaporate, and the molten phase is seeded before the η-anhydrate starts to crystallize with the seed crystals of the δ-anhydrate. Stirring may be of advantage. The time required depends on the amount of starting material used. Preferably wet tetrahydrate is used as starting material.

According to process (h) the heating time is from about 30 to about 100 hours depending on the temperature and on the amount of the starting material used and the thickness of the layer of the crystal powder. Preferably the starting material is heated for about 45 to 50 hours, at a relative humidity of about 15% in a constant temperature humidity device and a thickness of the layer of the crystal powder of about 3 to 4 cm.

Collecting the desired crystal forms according to processes (b) to (h) comprises the mechanical scratching off from the reaction vessel and the manual separation and picking out the desired crystals.

The pharmaceutical preparations comprising the novel crystal modifications of the invention are solid preparations such as powders, granules, tablets, coated tablets, suspensions and the like. In order to produce these pharmaceutical preparations, conventional pharmaceutically acceptable additives, such as vehicles, binders, lubricants, coating agents, coloring agents and perfumes can be used. Conventional formulating techniques are applied to the formulations.

For example, for the preparation of granules to be taken dry or in aqueous suspension the novel crystal modifications are extruded and dried, if desired in the form of vermicellis, ground with the help of an appropriate apparatus into fine particles measuring from 20 to 200 microns, preferably from 50 to 100 microns.

The active substance thus obtained is mixed with a viscosity-increasing agent, for example gum acacia, agar, polyvinylpyrrolidone, silicon dioxide, sodium carboxymethylcellulose, carboxymethyl starch, gum tragacanth, gum xanthene, gum guar, gum arabic, polyacrylic acid (Carbopol ®) etc. and with a sweetening agent, such as mannitol, sorbitol, xylitol, saccharose, sodium saccharine, sodium cyclamate, aspartum, fructose, hydrogenated glucose syrup (Lycasin ®) glucose, ammonium glycyrrhizinate, neohesperidine, dihydrochalcones or lactulose.

The mixture thus obtained is granulated in an air bed drier or in a planetary mixer and is extruded. For doing this, one can utilize binder solutions, for example a solution of polyvinylpyrrolidone, gelatine, starch paste, hydroxypropylmethylcellulose and methylcellulose of low viscosity, sodium carboxymethylcellulose, calcium carboxymethylcellulose, polyvinylalcohols, copolymers of polyvinylpyrrolidone, vinyl acetate, etc. In the case of granulation in an air bed drier, granules are formed in the course of the nebulisation of the binder.

In the case of a classic granulation with the help of a planetary mixer, the pasty humid mass as formed is calibrated through an oscillating granulator with an appropriate sieve or is extruded through a perforated plate with an appropriate apparatus. The granules obtained are dried in a heated drying stove or in an air bed drier and calibrated to granules with a particle diameter of 100 to 1000 microns, preferably from 200 to 700 microns. These granules are mixed with antistatic flowing agents, for example talcum, silicon dioxide, kaolin and others, and optionally with an aroma substance for giving them a pleasant taste, for example a banana aroma, a cherry aroma, a raspberry aroma, etc. The mixture thus obtained is filled into unit dosage sachets, containing a single dosage of active ingredient. It can also be filled into a multidosage package, from which the single doses are separated with the help of a measuring devise.

It is preferred to use mannitol in combination with sodium saccharine or sodium cyclamate as sweetening agent in a proportion of 1 part of active substance for 2 parts of mannitol. However, this relation may vary from 1 to 1 to 1 to 10 parts of mannitol. As a suspension agent one uses carboxymethyl starch in a concentration which can vary from 10 parts to 1 part of the active substance for 1 part to 10 parts of carboxymethyl starch respectively, and preferably in a concentration of 2 parts of active substance for 1 part of carboxymethyl starch.

For manufacturing tablets by direct compression the new crystal modifications are extruded and dried, if desired in the form of vermicellis, calibrated through a sieve of 1 mm and mixed with excipients utilisable for the direct tabletting, for example microcrystalline, cellulose, atomised lactoce, dicalcium phosphate (Emcompress ®), spray crystallized maltose or dextrose (Emdex ®), maize starch polymer (STA-RX ®) or others. These constituents can vary percentagewise from 5–50% with respect to the active substance and can be mixed also with a filler in the order of 1–20%, for example carboxymethyl starch, polyvinyl pyrrolidone (Polyplasdon ®XL), gum guar, sodium carboxymethylcellulose of low viscosity, hydroxypropylcellulose of low viscosity, crosslinked sodium carboxymethylcellulose, alginates, etc.

In addition, one can incorporate a lubricant in an amount of 0.1 to 5% in order to avoid the sticking of the tablets to the tablet stamps and improve the free flow thereof, for example talc, magnesium stearate, mixture of mono-, di- and tri-esters of palmitinic and stearinic acid with glycerol (Precirol ®), polyethyleneglycole, stearic acid, hydrogenated castor oil, sodium chloride, DL-Leucine, sodium oleate, sodium lauryl sulphate, silica gel (Cab-O-Soil ® or Aerosil ®), etc.

For the tabletting by granulation the novel crystal forms are centrifuged and dried in the form of powder, mixed with diluent, for example lactose, microcrystalline cellulose, etc. and with a filler, for example carboxymethyl starch, starch, carboxymethyl cellulose of low viscosity and others; and the mixture thus obtained is kneaded with a solution of a binder in water, for example a solution of gelatin, of of polyvinyl alcohol etc., and granulated through an oscillating granulator or through an extruder and dried in an air bed drier.

The granules obtained are calibrated through a sieve and mixed with a lubricant, for example magnesium stearate, talc, sodium lauryl sulphate, etc. With the help of an eccentric or rotative tabletting machine, this mixture is used for the preparation of the tablets.

The tablets obtained can be coated with film-forming solutions suitable in the pharmaceutical technology (film-coating), be it with organic solvents, be it without organic solvents. For the film-coating of these tablets on the basis of organic solvents, film-forming agents like gum lac and hydroxypropylmethyl cellulose of low viscosity can be used. On the other hand, for the coating without organic solvents, one uses film-forming substances on the basis of hydroxypropylmethyl-cellulose, polyethylenglycol or a latex like the copolymers of acrylic and methacrylic acid (Eudragit ®E-30-D) or of ethylcellulose (Aquacoat-EDC-30 ®) with a certain number of plastifiers like triacetine, polyethyleneglycol, hydroxypropylmethyl cellulose, pigments, for example titanium dioxide, talc, colorants, on the basis of iron oxides and Vitamin A (Ariavit ®). It is also usual to use antifoaming agents and wetting agents.

For manufacturing capsules the two methods described preceedingly are common, be it by direct compression, be it by the humid granulation as described. The same granules can be used with small quality of lubricant for the filling of the hard gelatin capsules with an apparatus which is normally used for the preparation of this galenic form.

The FIGS. 1, 2 and 3 of the accompanying drawings show, that the α-monohydrate of the invention has a high stability to moisture and is also more stable to light than known crystal forms of (+)-catechin. This means, that the α-monohydrate has caracteristics very advantageous for formulation into pharmaceutical preparations or for storage, e.g. in the form of pharmaceutical preparations (see Table 3 and FIG. 3).

FIG. 1 of the accompanying drawing shows the water content behavior of the α-monohydrate of the invention which does not depend upon the moisture content of the atmosphere. It is seen from FIG. 1, that the δ-anhydrate readily changes to the α-monohydrate, but the α-monohydrate scarcely shows any change in water content or does not show any substantial change in water content at a low (relative humidity 0 to 20%) or at a high humidity (relative humidity more than 60%).

FIG. 4 of the accompanying drawings likewise shows the water content behavior of the known tetrahydrate, β-monohydrate and η-anhydrate which changes with the moisture content of the atmosphere. It is seen from FIG. 4, that these known hydrate and anhydrate forms easily change the water content according to the moisture content of the atmosphere.

FIG. 2 of the accompanying drawings shows the stability of the β-monohydrate and the α-monohydrate to ultraviolet light exposure. It is seen, that the β-monohydrate is colored (turns from white to brown) upon ultraviolet irradiation, whereas the α-monohydrate does not as readily color upon ultraviolet irradiation (see Example 4 given hereinbelow and FIG. 2).

In the preparation of pharmaceutical preparations, the novel (+)-catechin crystal forms, especially the α-monohydrate, of this invention show great and decisive advantages over the known forms. Firstly, since the α-monohydrate is stable to moisture (water), no cumbersome control of ambient humidity (water content) is required during the preparation of the pharmaceutical compositions and during storage, particularly of the latter. Furthermore, pharmaceutical preparations having a constant content of the active ingredient ((+)-catechin) can be prepared. In addition, unlike pharmaceutical preparations comprising the known β-monohydrate, the solid pharmaceutical preparations comprising the novel crystal modifications of the invention undergo little variations in weight, thickness and hardness and are very stable (see Example I and Table 3). The dissolution behavior of the active ingredient from the pharmaceutical compositions is not affected (see Example 7, Table 4) and the latter are stable to ultraviolet light (see Example H and FIG. 3). The bioavailability e.g. of the novel α-monohydrate of the invention is the same as that of the known β-monohydrate (see Referential Example 2 and FIG. 5).

The novel α-monohydrate, if crystallised according to process (a) from hot water, or prepared form an aqueous suspension according to process (b) has a much less bitter taste than the hitherto known forms. This indicates, that through this procedure the bitter principles usually accompanying (+)-catechin are removed.

The α-monohydrate, as well as the γ- and δ-anhydrate, and pharmaceutical preparations comprising them in accordance with this invention can be applied for the same therapeutic purposes and according to the same methods of administration and in the same dosages (calculated on (+)-catechin) as the ones comprising the known tetrahydrate or β-monohydrate.

For example, in the treatment of acute hepatitis, the novel crystal modifications are administrered orally in dosages of about 1.5 to about 3.0 g (calculated as anhydrous (+)-catechin) per day to a patient once or in two or three portions.

The following Examples and Referential Examples illustrate the present invention and its advantages in more detail.

The following abreviations are used: HPLC: high pressure liquid chromatography; Column RP Types, solvent methanol/acetic acid/water 250:10:1000; TLC; thin-layer-chromatography; on cellulose with solvent system water/dioxan 100:10.

EXAMPLE 1

(a) A stirred solution of prepurified (+)-catechin tetrahydrate in water (4000 l, containing 10.5% anhydrous (+)-catechin) is cooled within 3-4 hours from 75° C. to 50° C. At 65° C. 1 kg of α-monohydrate seed crystals are added. The reaction vessel is flushed with nitrogen (1.2-1.3 bar) and under continuous stirring allowed to cool to 20° C. When the crystallization has ceased the suspension is centrifuged for about 30 minutes whereupon the water content of the obtained α-monohydrate crystals is 21.6%. The drying is continued in an air bed drier for about one hour at 50° C., whereupon the temperature is raised for a few minutes up to 100° C. The end point of the drying is reached, when the crystals contain only one mole of water (control by the Karl-Fischer method). The obtained (+)-catechin α-monohydrate has the following properties:

$[\alpha]_D^{20} = +15°$ (water-acetone 1:1 v/v).

Water content: calculated: 5.85%, found: 6.23% (Karl Fisher).

HPLC: 101.3% (+)-catechin (calculated on anhydrous forms) and less than 0.1% epicatechin; no other impurities according to HPLC or TLC; the X-ray powder diagram indicates the presence of the α-monohydrate.

The lattice distances in Angstrom (Å) of the X-ray diffraction spectrum of the obtained (+)-catechin αmonohydrate (as powder) are calculated from the diffraction lines of the Cu:$K_{\alpha l}$-rays ($\lambda = 1.5405$ Å) recorded on a film with the aid of a Guinier IV camera. As a standard there is used α-quartz, the d-values of which are calculated from $a_o = 4.913$ Å and $c_o = 5.405$ Å. The relative intensities of the lines are estimated by inspection with the eyes. The following lattice distances and relative intensities are obtained:

| Lattice Distances in Å | Relative Intensities |
| --- | --- |
| 7.1 | strong |
| 6.2 | medium |
| 5.95 | weak |
| 4.49 | strong |
| 4.38 | weak |
| 4.20 | strong |
| 4.13 | very strong |
| 3.97 | strong |
| 3.84 | medium |
| 3.78 | medium |
| 3.75 | weak |
| 3.65 | very strong |
| 3.58 | medium |
| 3.41 | strong |
| 3.37 | weak |
| 3.24 | medium |
| 3.18 | medium |

The α-monohydrate is characterized by thermogravimetry, whereby the loss of water upon heating of a sample at a rate of 5° C. per minute in a normal air atmosphere at discrete temperatures is gravimetrically determined, as follows:

| Temperature | Weight Loss as Water in % |
| --- | --- |
| 30 | 0 |
| 40 | 0 |
| 50 | 0.01 |
| 60 | 0.03 |
| 70 | 0.05 |
| 80 | 0.08 |
| 90 | 0.14 |
| 100 | 0.22 |
| 110 | 0.41 |
| 120 | 1.06 |
| 130 | 2.47 |
| 140 | 4.30 |
| 150 | 5.68 |
| 160 | 5.90 |
| 170 | 5.93 |
| 180 | 5.95 |

If, instead of the α-monohydrate, the tetrahydrate or the β-monohydrate or mixtures thereof should be obtained, the starting material may have to be further purified, finer and/or more seed crystals (more seed germs) to be applied, and/or the cooling time after seeding to be prolonged in order to assure the crystallisation of the α-monohydrate.

(b) A stirred solution of pure(+)catechin tetrahydrate in water (543 g solution, containing 18.4% anhydrous (+)-catechin) is kept for 5 minutes at 87.5° C. as a clear solution and allowed to cool to 69° C. within 25 minutes. 2.17 g of α-monohydrate as a fine crystal powder (particle size of the crystals smaller than 10 μm) are added as seed crystals.

The temperature is kept for 18 minutes at 69° C. A marked cristallisation is observed.

The temperature is lowered stepwise according to the following program:

| Time after seeding in h | Temperature in °C. | Concentration of anhydrous (+)catechin in the mother liquor |
|---|---|---|
| 0 | 69 | 18.4 |
| 0.3 | 68.8 | 8.1 |
| 1.0 | 59.7 | 4.5 |
| 1.7 | 50.9 | 2.9 |
| 2.7 | 22.5 | 1.3 |

The suspension is filtered and the obtained crystals are spread out and air dried at room temperature. The X-ray diffraction spectrum and the thermogravimetry is in agreement with the α-monohydrate.

Form of the crystals: fine, slightly yellow needles.

Water content according to thermogravimetry: 5.9%.

The taste of the obtained α-monohydrate as powder and in aqueous solution is extremely mild compared with the taste of representative samples of the β-monohydrate.

EXAMPLE 2

A suspension of 27.5 g of (+)-catechin tetrahydrate (wet centrifuged tetrahydrate with a water content of 37%) in 100 ml of water is heated up to 59.5° C. for 22 hours. The crystals are filtered of and air dried to give 12.6 g of (+)-catechin α-monohydrate. The X-ray diffraction spectrum and the thermogravimetry is in agreement with the α-monohydrate:

| Lattice distance in Å | Relative Intensities |
|---|---|
| 7.2 | very strong |
| 6.2 | medium |
| 5.95 | medium |
| 4.49 | very strong |
| 4.39 | medium |
| 4.20 | strong |
| 4.13 | strong |
| 3.97 | strong |
| 3.84 | medium |
| 3.78 | medium |
| 3.75 | medium |
| 3.65 | strong |
| 3.58 | medium |
| 3.41 | medium |
| 3.37 | weak |
| 3.24 | medium |
| 3.19 | medium |

Thermogravimetry:

| Temperature in °C. | Weight Loss as Water in % |
|---|---|
| 30 | 0.03 |
| 40 | 0.03 |
| 50 | 0.05 |
| 60 | 0.05 |
| 70 | 0.08 |
| 80 | 0.10 |
| 90 | 0.12 |
| 100 | 0.18 |
| 110 | 0.25 |
| 120 | 0.71 |
| 130 | 2.03 |
| 140 | 3.77 |
| 150 | 5.50 |
| 160 | 5.77 |
| 170 | 5.79 |
| 180 | 5.81 |

TLC: no decomposition products detectable.

The optical rotation is identical with the one given in Example 1.

EXAMPLE 3

In a pressure capsule which withstands vapor pressures of up to 30 bars a sample of 53 mg of (+)-catechin β-monohydrate is heated in a DSC-2C (Differential Scanning Calorimeter of the Perkin-Elmer Corp.) with a rate of 10° C. per minute up to a temperature of 126° C. After the immediate cooling (cooling rate 320° C./min) the sample showed the X-ray diffraction spectrum of the α-monohydrate. TLC: no decomposition products detectable; thermogravimetry indicates presence of α-monohydrate.

EXAMPLE 4

(+)-Catechin tetrahydrate, produced by the method described in Chemische Berichte 36, 101–107 (1903), is pulverized to a size of 10 microns, and 400 g of the powder is spread in a constant temperature-humidity device (Model PR-3A made by Tabai Seisakusho K.K.) so that the powder layer has a thickness of 3 to 4 cm. The powder is left to stand overnight at a temperature of 70° C. and a relative humidity of 80% to give the α-monohydrate having the following properties:

Form: white needles.

Elemental analysis for $C_{15}H_{14}O_6 \cdot H_2O$: Calculated: C: 58.44%, H: 5.23%, Found: C: 58.35%, H: 5.09%.

Water content: Calculated: 5.84%, Found: 5.72%.

X-ray diffraction spectrum as shown hereinbefore.

α-Monohydrate having the same property values as above is also obtained when the β-monohydrate or η-anhydrate produced in accordance with the method described in Chemische Berichte 36, 101–107 (1903), is used as the starting material.

For the manufacturing methods and physical property values of the tetrahydrate, the β-monohydrate and the η-anhydrate used above, see Referential Example 1 given hereinbelow.

FIG. 1 of the accompanying drawings shows the changes in the water content (shown on the ordinate) of the α-monohydrate of the invention (the line obtained by connecting the dots in FIG. 1) depending upon the moisture content of the ambient atmosphere (20° C.) (indicated as the relative humidity on the abscissa of FIG. 1). The experiment was conducted as follows: One gram of the sample was taken into a weighing bottle and left to stand for two weeks at 20° C. in a desiccator whose moisture content was adjusted by using a saturated aqueous solution of each of the salts having the relative humidities shown below. Then, the water content of the sample was measured by the Karl-Fischer method.

| Relative Humidity (%) | Salt |
|---|---|
| 12 | LiCl |
| 23 | CH₃COOK |
| 33 | MgCl₂ |
| 44 | K₂CO₃ |
| 57 | NaBr |
| 68 | CuCl₂ |
| 75 | NaCl |
| 84 | KBr |
| 94 | KNO₃ |

It is seen from FIG. 1 that the water content of the monohydrate in the new crystal form in accordance with this invention scarcely changes with changes in the humidity of the atmosphere.

FIG. 2 of the accompanying drawings shows the stability of the α-monohydrate of the invention (the line obtained by connecting the dots in FIG. 2) to ultraviolet light together with the stability of the known β-monohydrate (the line obtained by connecting the small circles). The experiment was performed as follows: Six grams of the sample was filled in a cell for powder measurement of a color difference meter (a digital color and color difference meter, Model ND-101D, made by Nippon Denshoku Kogyo K.K.), and placed about 10 cm below a high-pressure mercury lamp (300 W high-pressure mercury lamp made by Eikosha K.K.) and exposed to light irradiation. The cell was periodically taken out, and the Hunter's L, a and b values were measured by the color difference meter. The Hunter's color difference (ΔE) was calculated in accordance with the following equation.

$$\Delta E = \sqrt{(\Delta a)^2 + (\Delta b)^2 + (\Delta L)^2}$$

As shown in FIG. 2, the degree of coloration (white to brown) upon light irradiation of the α-monohydrate is smaller than that of the β-monohydrate, and therefore the former has better stability to light.

The α-monohydrate is chemically the same substance as the known β-monohydrate as is clearly seen from Table 1 below.

TABLE 1

| Test item | β-monohydrate | α-monohydrate |
|---|---|---|
| Elemental analysis | | |
| Found | C 58.20%, H 5.10% | C 58.35%, H 5.09% |
| Calculated | C 58.44%, H 5.23% | C 58.44%, H 5.23% |
| Water content (*1) | | |
| Found | 5.80% | 5.72% |
| Calculated | 5.84% | 5.84% |
| UV spectrum (*2) | λmax 280 nm | λmax 280 nm |
| | λmin 250 nm | λmin 250 nm |
| Thin-layer chromatogram (*3) | A single spot appeared at Rf = 0.65 | A single spot appeared at Rf = 0.65 |
| Gas chromatogram (*4) | A single peak appeared at Rt = 11.5 minutes | A single peak appeared at Rt = 11.5 minutes |
| Specific rotation $[\alpha]_D^{20}$ (*5) | +15.2° | +15.2° |

(*1): Measured by the Karl-Fischer moisture content meter.
(*2): UV spectrum was measured with regard to an ethanol solution (1→20,000) of the sample using ethanol as a control
(*3): Thin-layer chromatogram
Thin-layer plate: prepared by using cellulose for thin-layer chromatography (DC Fertig Platten Cellulose, made by Merck & Co.)
Developed solvent: Dioxane/acetic acid/water (1:1:10)
Method of detection: A 10% aqueous solution of sodium carbonate and a 0.5% aqueous solution of Fast Blue B Salt were sprayed.
(*4): Gas chromatogram
Separating column: 2% silicone UC, 2 m
Column temperature: 250° C.
Carrier gas: nitrogen 50 ml/min.
The sample was chromatographed after it was trimethylsilylated.
(*5): Measured by using a 50% aqueous solution of acetone.

EXAMPLE 5

(1) The β-monohydrate is pulverized to size of 10 microns and 400 g of the powder is spread in a constant temperature-humidity device in a layer having a thickness of 3 to 4 cm, and then maintained at a temperature of 70° C. and a relative humidity of 15% for 48 hours to form The δ-anhydrate of the following properties:
Form: white needles.
Melting point: 203°–207° C. (decomp.).
Elemental analysis for $C_{15}H_{14}O_6$: Calculated: C: 62.07%, H: 4.86%, Found: C: 62.35%, H: 4.73%.
X-ray diffraction spectrum as shown hereinbefore.
FIG. 1 shows the changes of the water content of the δ-anhydrate (the line obtained by connecting the small circles in FIG. 1) depending upon the moisture content of the atmosphere (20° C.).

Table 2 below shows that the δ-anhydrate is chemically the same as the known η-anhydrate

TABLE 2

| Test item | η-anhydrate | δ-anhydrate |
|---|---|---|
| Elemental analysis | | |
| Found | C 62.37%, H 4.71% | C 62.35%, H 4.73% |
| Calculated | C 62.07%, H 4.86% | C 62.07%, H 4.86% |
| Water content (*1) | | |
| Found | 0.20% | 0.15% |
| Calculated | 0% | 0% |
| UV spectrum (*2) | λmax 280 nm | λmax 280 nm |
| | λmin 250 nm | λmin 250 nm |
| Thin-layer chromatogram (*3) | A single spot appeared at Rf = 0.65 | A single spot appeared at Rf = 0.65 |
| Gas chromatogram (*4) | A single peak appeared at Rt = 11.5 minutes | A single peak appeared at Rt = 11.5 minutes |
| Specific rotation $[\alpha]_D^{20}$ (*5) | +15.2° | +15.2° |

(*1) to (*5) are the same as in the footnote to Table 1.

(2) Fifty grams of the δ-anhydrate is placed in a constant temperature-humidity device, and maintained at a temperature of 60° C. and a relative humidity of 90% for 48 hours to form the α-monohydrate.

EXAMPLE 6

A sample of 3 g (+)-catechin β-monohydrate is heated in a drying oven at 112° C. during 70 hours, whereby 6.7% of water are lost. The obtained crystals of the (+)-catechin γ-anhydrate are cooled and give the X-ray powder diagram shown hereinbefore, indicating in addition the present of a trace of (+)-catechin δ-anhydrate.

The formation of the γ-anhydrate may be facilitated by carefully admixing seed crystals of the γ-anhydrate to the starting material. TLC: no decomposition detectable. The crystal modification and the chemical composition is stable for at least 10 month if stored in a closed powder bottle at room temperature and 58% relative humidity.

EXAMPLE 7

A sample of 3.08 g of a fine crystal powder of (+)-catechin tetrahydrate (wet centrifuged with a water content of 37%) in a glass beaker of about 4 cm diameter is heated in an oil bath at 147° C. The crystals melt within about five minutes. Upon stirring within another five minutes a solid phase is formed, which is cooled to room temperature, pulverized and analyzed. The X-ray powder diagram indicates the crystal form of the pure γ-anhydrate. Total water content (measured by a thermobalance): 1.9%; HPLC: 102.1% of anhydrous (+)-catechin and less then 0.1% epicatechin; TLC (silicagel/CHCL$_3$-ethylacetate-water-formic acid 5:5:0.3:1) no other impurities detectable.

If the thickness of the crystal melt is increased the heating time at 147° C. has to be prolonged until the water content of the crystals is near to zero.

EXAMPLE 8

A sample of 1 g of (+)-catechin η-anhydrate is heated in a drying oven for 23 hours at 112° C., whereby 4.4% of non-crystal (surface bound) water are lost. After cooling the X-ray powder diagram indicated the presence of (+)-catechin δ-anhydrate with a trace of the η-anhydrate. No decomposition products are detectable by TLC (Silicagel/CHCL$_3$-ethylacetate-water-formic acid 5:5:0.3:1). Total water content (measured by thermobalance): 0.5%.

EXAMPLE 9

A fine crystal powder of 3.03 g of (+)-catechin tetrahydrate (wet centrifuged tetrahydrate with a water content of 45%) in a glass beaker (4 cm diameter) is heated in an oil bath at 149° C. The crystals melt within about 1 minute to give a slightly yellow liquid. The free and the bound water is evaporated during the melting process. Seed crystals of the δ-anhydrate (50 mg) in form of a fine powder are added to the liquid, whereupon the melt crystallizes immediately. The obtained solid phase is cooled to room temperature, pulverized and analyzed. The X-ray powder diagram indicated as the main component the crystal form of the δ-anhydrate and as further components the α-monohydrate and the γ-anhydrate.

If the thickness of the crystal melt is encreased the heating time at 149° C. may have to be prolonged until the water content of the crystals is nearly zero.

EXAMPLE 10

A sample of (+)-catechin η-anhydrate is heated in a drying oven at 150°–170° C. for 30 minutes. The (+)-catechin γ-anhydrate is obtained with the following properties:

X-ray powder diagram (lattice distances in Å): 5.60±0.06; 4.63±0.05; 4.00±0.03; 3.81±0.03;
Form: needles.
Melting point: 200°–206° C. (decomp.)
Elemental analysis for $C_{16}H_{14}O_6$: calculated: C: 62.07%, H: 4.86%, found: C: 62.52%, H: 4.92%.

EXAMPLE A (SACHETS)

Ingredients for 1250 sachets:

| | |
|---|---|
| (1) mannitol | 2500 g |
| (2) carboxymethyl starch | 625 g |
| (3) (+)-catechin α-monohydrate | 1250 g |
| (4) sodium saccharine | 50 g |
| (5) banana aroma in powder | 125 g |
| (6) water | |

In the Examples A–B the sequence of the process steps is the following: (1), (2) and (3) are mixed in a planetary mixer during 20 minutes and the solution of (4) in (6) is poured on to the mixture as prepared and kneaded during 20 minutes. The pasty mixture obtained is calibrated through a sieve of 2.5 mm and dried in an air drier during 20 minutes at 60° C.

The dried granules are calibrated through a sieve of 1 mm and then mixed with banana aroma in a planetary mixer.

With the help of a suitable apparatus the sachets are filled and thermowelded. The sachets contain each 1000 mg of (+)-catechin α-monohydrate per dosage of 3.64 g of granulated powder.

EXAMPLE B (SACHETS)

In analogy to Example A the following ingredients are compounded into a granulated powder and filled into 1250 sachets:

| | |
|---|---|
| (1) sorbitol | 2500 g |
| (2) carboxymethylcellulose | 625 g |
| (3) (+)-catechin α-monohydrate | 1250 g |
| (4) sodium cyclamate | 50 g |
| (5) raspberry aroma | 125 g |
| (6) water | 1875 g |

EXAMPLE C (SACHETS)

In analogy to Example A the following ingredients are compounded into a granulated powder and filled into 1250 satchets:

| | |
|---|---|
| (1) fructose | 2500 g |
| (2) carboxymethylcellulose | 625 g |
| (3) (+)-catechin α-monohydrate | 1250 g |
| (4) sodium cyclamate | 50 g |
| (5) cherry aroma | 125 g |
| (6) water | 1875 g |

EXAMPLE D (TABLETS)

Ingredients for 100'000 tablets:

| | |
|---|---|
| (1) (+)-catechin α-monohydrate | 50,0 kg |
| (2) carboxymethyl starch | 2,0 kg |
| (3) silicon dioxide (Aerosil ® -200) | 0,5 kg |
| (4) magnesium stearate | 0,25 kg |
| (5) microcrystalline cellulose (Avicel ® -102 | 5,0 kg |
| | 57,75 kg |

The vermicellis of (+)-catechin α-monohydrate are calibrated through a sieve of 1 mm mounted on an oscillating calibrator. In a drum mixer the active substance is mixed during 20 minutes with carboxymethyl starch (2), silicon dioxide (3) and the microcrystalline cellulose (5):

then the magnesium stearate (4) is added and the mixing process continued for 5 more minutes. The mixture is used for the preparation of round biconvex tablets with a weight of 577,5 mg/tablet and a diameter of 10,5 mm. The hardness of these tablets is between 130–180N (Heberlein) and the disintegration in the artificial gastric juice (pH 1,2; Pharmacopée Helv. VI) is below 15 minutes. A rotating tabletting machine is used for making these tablets.

EXAMPLE E (TABLETS)

Ingredients for 100'000 tablets:

| | | |
|---|---|---|
| (1) (+)-catechin α-monohydrate | 50,0 kg | |
| (2) carboxymethyl starch | 1,0 kg | |
| (3) distilled water | (21,0) kg | |
| (4) silicon dioxide (Aerosil-200) | 0,25 kg | |
| (5) magnesium stearate | 0,25 kg | |

The (+)-catechin α-monohydrate is centrifuged and dried in the form of a powder, mixed with carboxymethyl starch (2) in a planetary mixer during 20 minutes, humidified with distilled water and kneaded during 20 minutes.

The pasty mass obtained is granulated through a sieve of 3.0 mm, mounted on an oscillating granulator, and dried in an air bed drier of 70° C. The granules obtained are calibrated through a sieve of 1.5 mm and mixed with silicon dioxide (4) and magnesium stearate (5) in a free-fall-mixer. The mixture thus obtained is compressed with the help of a rotative tabletting machine into round tablets of 515 mg/tablet of a hardness of 120–150N (Heberlein) and a disintegration rate in the artificial gastric juice (Pharm. Hel. VI) below 15 minutes.

EXAMPLE F (COATED TABLETS)

Ingredients for 10'000 tablets:

| Composition | dry substance per tablet (mg) | quantity for 10'000 tablets (g) |
|---|---|---|
| (1) Hydroxypropylmethyl-cellulose (Pharmacoat ® -603) | 12 | 120 |
| (2) Colorant suspension (25% dry material) | 3 | (120) |
| (3) Distilled water | — | 227,5 |
| (4) Talcum | 2,5 | 25 |
| Total | 17,5 | (492,5) |

| Composition of the colorant suspension | dry substance per tablet (mg) | quantity for 2,0 kg (g) |
|---|---|---|
| Hydroxypropylmethylcellulose (Pharmacoat ® -603) | 0,6 | 100 |
| Titanium dioxide | 2,4 | 400 |
| Distilled water | — | (1500) |
| Total | 3,0 | (2000) |

( ) = humid material

Preparation of the suspension

Pharmcoat ® is dispersed in water of 80° C.; titanium dioxide is added and both are homogenised in a Homorex ® mixer with helical spikes. The suspension thus obtained is passed on to a Dino-Mill ® (with recycling).

Preparation of the coating suspension

Pharmacoat ® is dispersed in water of 80° C., and the colorant suspension is added to the cooled dispersion under weak agitation.

Application

The colorant suspension is applied to the tablets by means of continuous nebulisation. The quantity of air blown in must maintain the tablets between 30°–35° C. during the application. The tablets are then dried in a turbine for 10 minutes and 50° C. under weak rotation.

The disintegration of these coated tablets in the artificial gastric juice (Pharm. Hel. VI) is below 60 minutes.

EXAMPLE G (CAPSULES)

Ingredients for 10'000 capsules:

| | | |
|---|---|---|
| (1) (+)-catechol α-monohydrate | 5'000 g | |
| (2) stearic acid | 30 g | |
| (3) magnesium stearate | 10 g | |

The vermicellis of (+)-catechin α-monohydrate are calibrated through a sieve of 1 mm and mixed with the stearic acid and magnesium stearate during 20 minutes.

This mixture is used for the preparation of the capsules of size O with 500 mg of active ingredient for the help of a suitable encapsulating apparatus.

The disintegration of these capsules in artificial gastric juice, (Pharm. Helv. VI) is below 15 minutes.

EXAMPLE H (POWDER)

Twenty grams of (+)-catechin α-monohydrate obtained in Example 4 were mixed with 20 g of lactose to form a powder (the pharmaceutical preparation A).

For comparison, 20 g of the (+)-catechin β-monohydrate were mixed with 20 g of lactose to form a powder (comparative pharmaceutical preparation A).

The pharmaceutical preparation A of the invention and the comparative pharmaceutical preparation A were each stored for one week at a temperature of 20° C. and a relative humidity of 84%, and changes in the weights of these preparations were examined. It was found that the pharmaceutical preparation A of the invention showed no change in weight, whereas the comparative pharmaceutical preparation A showed a weight increase of 8.8%. Hence, the preparation A of the invention has higher storage stability than the comparative pharmaceutical preparation A.

FIG. 3 of the accompanying drawings shows the stability of the pharmaceutical preparation A of the invention (the line obtained by connecting the dots in FIG. 3) to ultraviolet light together with that of the comparative pharmaceutical preparation A (the line obtained by connecting the small circles). The experiment was conducted in the same way as in Example 4. It is seen from FIG. 3 that the pharmaceutical preparation A of this invention has higher stability to ultraviolet light than the comparative pharmaceutical preparation A.

EXAMPLE I (TABLETS)

The (+)-catechin α-monohydrate crystals obtained in Example 4 were pulverized to a size of 10 microns, and 265 g of the resulting powder was mixed with 8 g of carboxymethyl cellulose calcium and 2 g of magnesium stearate. The mixture was tableted by means of a rotary tableting machine (with a punch of 9 mm φ and 11R; tablet weight 275 mg) to form tablets of a α-monohydrate (the pharmaceutical preparation B of the invention).

For comparison, the (+)-catechin β-monohydrate crystals were tableted in the same way as above to form tablets of the β-monohydrate (comparative pharmaceutical preparation B).

The pharmaceutical preparation B of the invention and the comparative pharmaceutical preparation B were each stored at a temperature of 20° C. and a relative humidity of 84%, and changes in the weight, thickness and hardness of each of the preparations were examined. The hardness was measured by means of a Erweka hardness tester (model TB 24, made by Erweka-Apparatebau). The results are shown in Table 3.

TABLE 3

| Tablet | Test item | Storage conditions and time | | |
|---|---|---|---|---|
| | | | 20° C./84% RH | |
| | | At the start of the test | 0.5 month | 1 month |
| Comparative preparation B β-monohydrate | Weight (mg) | 275.2 | 310.2 | 308.4 |
| | Thickness (mm) | 4.30 | 4.55 | 4.54 |
| | Hardness (kg) | 8.3 | 4.3 | 4.4 |
| Preparation B of the invention α-monohydrate | Weight (mg) | 275.1 | 276.0 | 275.8 |
| | Thickness (mm) | 4.31 | 4.32 | 4.32 |
| | Hardness (kg) | 9.6 | 9.0 | 8.9 |

As shown in Table 3, the pharmaceutical preparation B of the invention has higher storage stability than the comparative pharmaceutical preparation B.

EXAMPLE J (COATED TABLETS)

The tablets of the (+)-catechin monohydrate in the α-form (the pharmaceutical preparation B of the invention) obtained in Example I were coated with a coating solution consisting of 9 parts of hydroxypropyl methylcellulose, 1 part of titanium oxide and 90 parts of water at a rate of 11 mg per tablet. Thus, coated tablets of the α-monohydrate (the pharmaceutical preparation C of the invention) were obtained.

The pharmaceutical preparation C of the invention was stored at a temperature of 40° C. and a relative humidity of 80%, and the rate of dissolution of (+)-catechin from the tablets was examined.

The (+)-catechin dissolution test was carried out in the following manner. A test solution (JPX, first solution; one liter) and one test tablet were put in a dissolution test device (rotary basket method) set forth in Japanese Pharmacopoeia. The device was rotated at 100 rpm, and the contents were periodically sampled. The amount of (+)-catechin was determined by spectrophotometry. The results of the dissolution test are shown in Table 4.

TABLE 4

| | Dissolution time (t$_{50}$) (*1) | | |
|---|---|---|---|
| | Storage conditions and time | | |
| | At the start | 40° C./75% RH | |
| Coated tablets | of the test | 0.5 month | 1 month |
| Preparation C of the invention | 8.0 minutes | 8.2 minutes | 7.8 minutes |

(*1): The time which elapsed until the (+)-catechin dissolved in an amount of 50% in the test solution from the test tablet.

EXAMPLE K

Sachets, tablets, coated tablets, capsules and powders can be prepared in an analogous manner as described in Examples A to J, if instead of (+)-catechin-α-monohydrate, (+)catechin γ-anhydrate or (+)-catechin γ-anhydrate is used.

REFERENTIAL EXAMPLE 1 (Production of (+)-catechin tetrahydrate, β-monohydrate and η-anhydrate)

(1) Production of (+)-catechin tetrahydrate:

Crude catechin (500 g) was dissolved in 5000 ml of water under heat. The solution was allowed to cool, and the precipitated crystals were collected by filtration. The crystals were dried by passing air at room temperature for 4 hours to give the tetrahydrate crystals. Form: white needles Melting point: 95°–96° C.

Elemental analysis for $C_{15}H_{14}O_6.4H_2O$: Calculated: C: 49.72%, H: 6.12%, Found: C: 49.52%, H: 6.07%.

Water content: Calculated: 19.89%, Found: 20.05%.

X-ray diffraction spectrum as shown hereinbefore.

(2) Production of (+)-catechin β-monohydrate:

(+)-catechin tetrahydrate crystals (400 g) were dried in a sulfuric acid desiccator at room temperature and atmospheric pressure for two days to give the β-monohydrate crystals.

Form: white needles.

Melting point: 170°–177° C.

Elemental analysis for $C_{15}H_{14}O_6.H_2O$: Calculated: C: 58.44%, H: 5.23%, Found: C: 58.20%, H: 5.10%.

Water content: Calculated: 5.84%, Found: 5.80%.

X-ray diffraction spectrum as shown hereinbefore.

(3) Production of (+)-catechin η-anhydrate:

The tetrahydrate crystals were dried by passing air at 100° C. for 2 hours.

Form: white needles.

Melting point: 205°–210° C. (decomp.).

elemental analysis for $C_{15}H_{14}O_6$: Calculated: C: 62.07%, H: 4.86%, Found: C: 62.37%, H: 4.17%.

Water content: Calculated: 0%, Found: 0.2%.

X-ray diffraction spectrum as shown hereinbefore.

FIG. 4 shows changes in the water contents (the ordinate in FIG. 4) of the tetrahydrate (the line obtained by connecting the dots in FIG. 4), the β-monohydrate (the line obtained by connecting the small circles in FIG. 4), and the η-anhydrate (the line obtained by connecting the small triangles in FIG. 4) depending upon the moisture content (indicated as the relative humidity on the abscissa in FIG. 4) of the atmosphere (20° C.). The experiment was performed under the same conditions as shown in Example 1. It is seen from FIG. 4 that the water content of the tetrahydrate gradually decreases with decreasing humidity of the atmosphere, and the water contents of the β-monohydrate and η-anhydrate gradually increase with increasing humidity of the atmosphere until they change to the tetrahydrate.

REFERENTIAL EXAMPLE 2 (Absorption-excretion test)

Male Beagle dogs having a body weight of 10 to 11 kg, four per group, were fasted for one day, and 500 mg, calculated as anhydrate, of each of the α-monohydrate, the tetrahydrate and the β-monohydrate were orally administered to the dogs by a crossover method. After 0.5, 1, 2, 3, 4 and 6 hours from the administration, about 3 ml of the blood was sampled from the animals each time, and centrifuged. One milliliter of the plasma was taken, and 2 ml of an acetate buffer (pH 5.0) and 5 ml of ethyl acetate were added. The mixture was shaken. Then, 4 ml of the ethyl acetate layer as an upper layer was taken out, and evaporated. To the resulting solid 30 microliters of pyridine and 50 microliters of bis-TMS-trifluoroacetamide was added. The mixture was injected into a gas chromatograph (Gas Chromatograph Model 163, a product of Hitachi Limited; column 2% OV-1, 2 m; column temperature 280° C., carrier gas nitrogen 30 ml/min.). The catechin concentration in the plasma was calculated from the peak height of the resulting gas chromatogram (Rt=4.5 minutes).

The results are shown in FIG. 5. In FIG. 5, the abscissa represents the time (hours) of blood sampling after the administration, and the ordinate, the catechin concentration (μg/ml) of the plasma. In FIG. 5, the dots show the results obtained with regard to the α-monohydrate; and the small circles and triangles, the results obtained with regard to the β-monohydrate and tetrahydrate, respectively.

FIG. 5 shows that the α-monohydrate, tetrahydrate and β-monohydrate have the same plasma concentration pattern and no appreciable difference exists between them. Accordingly, they show equivalent bioavailability.

(4) Brief Description of the Drawings:

FIG. 5 is a graph showing changes in the plasma concentrations of the α-monohydrate of the invention and the known tetrahydrate and β-monohydrate upon oral administration.

Figure 1:
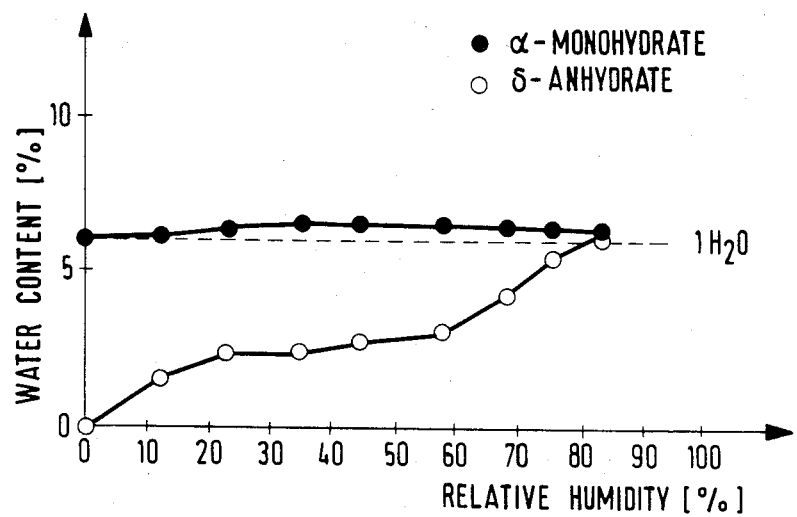
FIG. 1 is a graph showing the relation of changes in the water contents of the α-monohydrate and the δ-anhydrate of the invention to the humidity of the atmosphere in which they were maintained.
Figure 2:
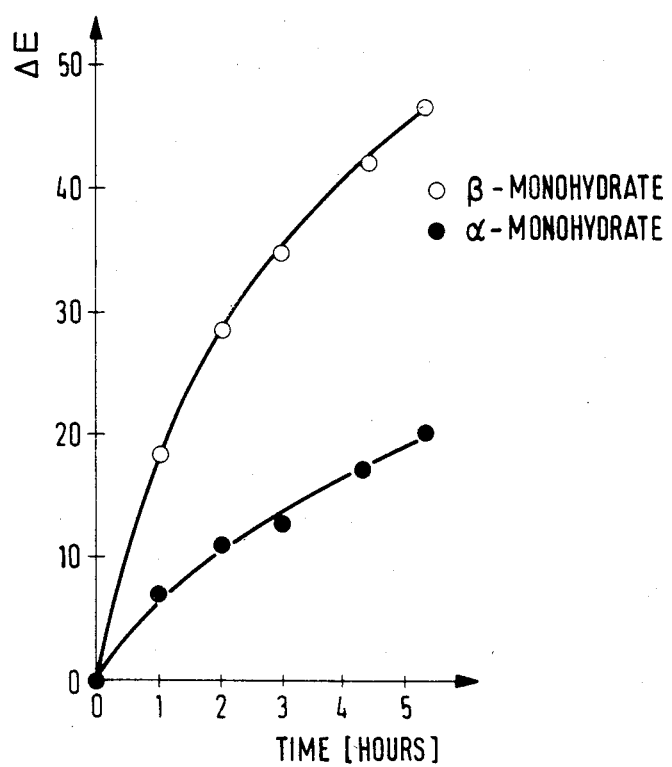
FIG. 2 is a graph showing changes in color of the α-monohydrate of the invention and the known β-monohydrate upon ultraviolet light irradiation.
Figure 3:
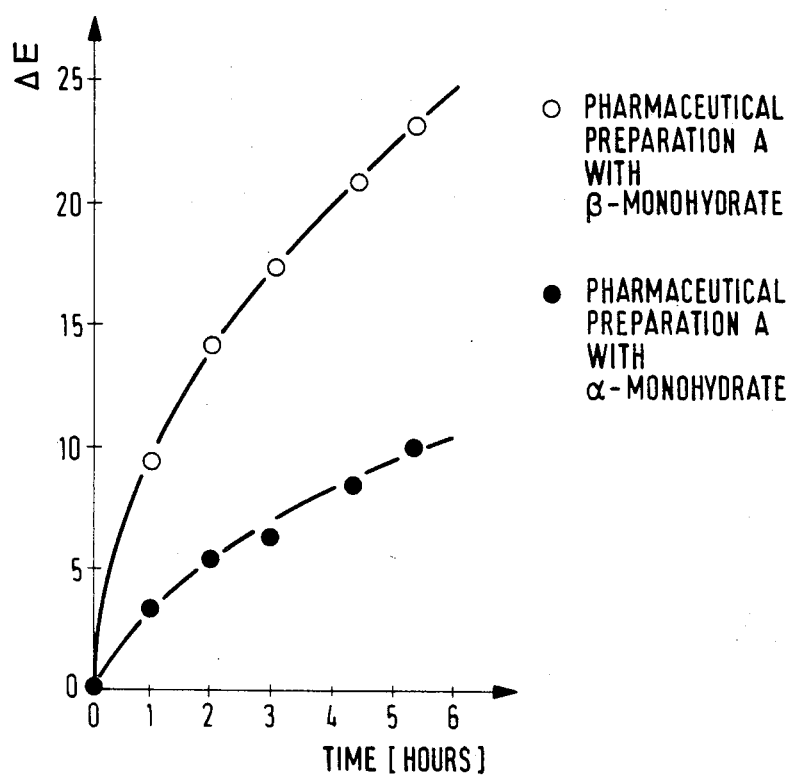
FIG. 3 is a graph showing changes in color of a pharmaceutical preparation containing the α-monohydrate of the invention and a pharmaceutical preparation containing the known β-monohydrate.
Figure 4:
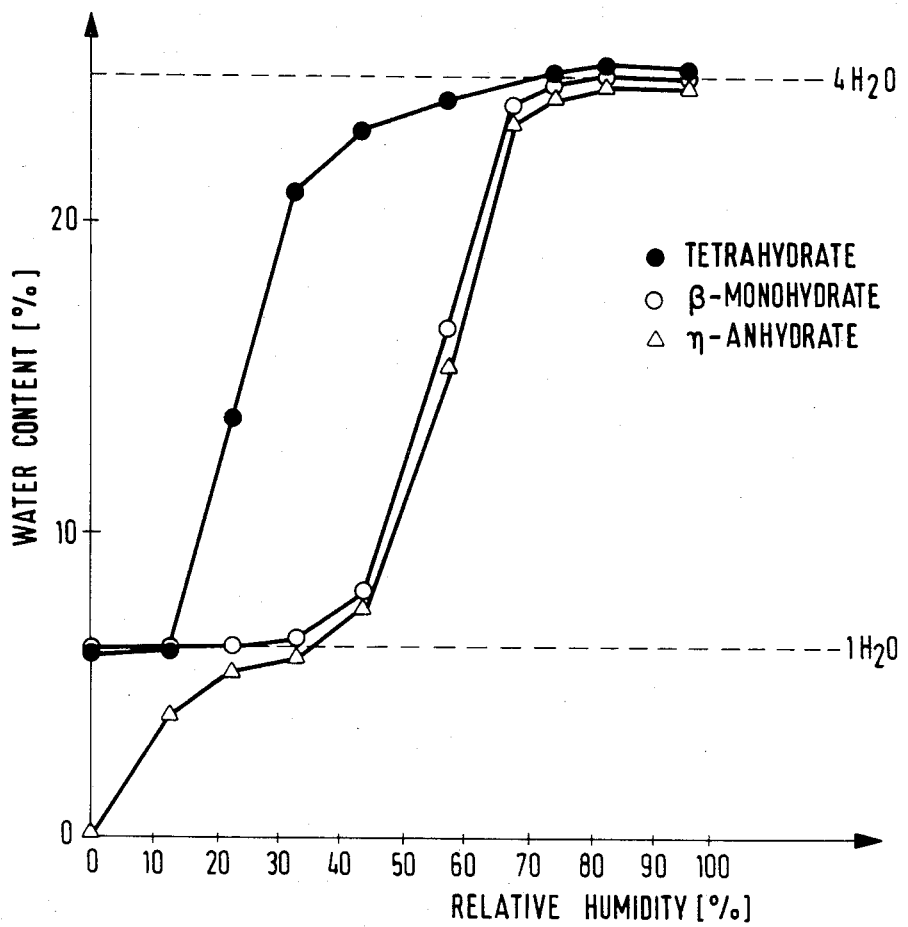
FIG. 4 is a graph showing the relation of changes in the water contents of the known tetrahydrate, β-monohydrate and η-anhydrate to the humidity of the atmosphere in which they were maintained.

What is claimed is:

1. (+)-Catechin α-monohydrate in a crystal form, which is free of substantially free from other known crystalline forms of (+)-catechin, and which is characterized by having an X-ray powder diffraction spectra obtained by using $Cu:K_{\alpha 1}$-rays, the following seventeen lattice distances and relative intensities:

| Lattice Distance in Å | Relative Intensities |
|---|---|
| 7.17 ± 0.10 | very strong |
| 6.17 ± 0.06 | medium |
| 5.95 ± 0.06 | medium |
| 4.49 ± 0.04 | strong |
| 4.39 ± 0.04 | medium |
| 4.20 ± 0.04 | strong |
| 4.13 ± 0.04 | strong |
| 3.97 ± 0.03 | medium |
| 3.84 ± 0.03 | strong |
| 3.78 ± 0.03 | medium |
| 3.75 ± 0.03 | medium |
| 3.65 ± 0.03 | very strong |
| 3.58 ± 0.03 | medium |
| 3.41 ± 0.02 | medium |
| 3.37 ± 0.02 | medium |
| 3.24 ± 0.02 | medium |
| 3.19 ± 0.02 | medium. |

2. In a method of treating hepatitis with an effective amount of a crystalline form of (+)-catechin, the improvement wherein the (+)-catechin is a crystal modification of (+)-catechin monohydrate according to claim 1.

3. A pharmaceutical composition for the treatment of hepatitis containing an effective amount of a crystal modification of (+)-catechin monohydrate according to claim 1, and a pharmaceutically acceptable carrier.

* * * * *